(12) United States Patent
Hutton

(10) Patent No.: US 7,780,594 B2
(45) Date of Patent: Aug. 24, 2010

(54) RETRACTOR AND METHODS OF USE

(75) Inventor: Clark Hutton, San Clemente, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 444 days.

(21) Appl. No.: 11/544,890

(22) Filed: Oct. 6, 2006

(65) Prior Publication Data

US 2007/0118022 A1 May 24, 2007

Related U.S. Application Data

(60) Provisional application No. 60/725,007, filed on Oct. 7, 2005.

(51) Int. Cl.
*A61B 1/32* (2006.01)
(52) U.S. Cl. ............... 600/219; 600/214; 600/215; 600/224
(58) Field of Classification Search ......... 600/184–246, 600/249
See application file for complete search history.

(56) References Cited

U.S. PATENT DOCUMENTS

| 4,130,113 | A | 12/1978 | Graham |
| 7,195,592 | B2 * | 3/2007 | Ravikumar et al. ......... 600/219 |
| 2005/0165281 | A1 | 7/2005 | Ravikumar et al. |
| 2006/0004261 | A1 * | 1/2006 | Douglas .................... 600/210 |

FOREIGN PATENT DOCUMENTS

| FR | 542 744 A | 8/1922 |
| WO | WO 01/03586 | 1/2001 |
| WO | WO 01/28431 A | 4/2001 |

OTHER PUBLICATIONS

International Search Report from PCT Application No. PCT/US2006/039409, Dec. 13, 2006.

* cited by examiner

*Primary Examiner*—Eduardo C Robert
*Assistant Examiner*—Christina Negrelli
(74) *Attorney, Agent, or Firm*—Michael R. Shevlin

(57) ABSTRACT

A retractor is disclosed. The retractor includes a housing, at least one blade holder slidably coupled to the housing, and an actuator handle to control sliding movement of the blade holder. The blade holder and the actuator handle hold at least one blade.

13 Claims, 4 Drawing Sheets

RETRACTOR AND METHODS OF USE

CROSS-REFERENCE TO RELATED APPLICATIONS

The present application claims priority to U.S. Provisional Application No. 60/725,007, to Hutton, filed Oct. 7, 2005, and titled "Retractor" and incorporates its entire disclosure herein by reference.

BACKGROUND OF THE INVENTION

1. Field of the Invention

The present invention relates generally to the field of surgery, and more specifically to a retractor device which may be used during spinal surgery for exposure of a surgical site.

2. Background of the Invention

There is a significant number of people that suffer spinal disorders that may require spinal surgery and/or intervention. Such surgeries typically require exposure and access to the internal spinal elements. Through the exposure, the surgeon may remove, add, medicate, and/or modify pathological elements to remedy the spinal disorder.

Conventional treatment may also include traction, either with a halter or with Crutchfield type tongs, followed by an application of a cast or a brace. If surgery is necessary, the area of injury is often fixed with a wire to allow fusion of the vertebrae in the affected region of the vertebral column. Often treatment also includes anterior decompression and fusion, or more recently, plates and screws to immobilize the unstable region. Such plates may be used either anteriorly or posteriorly, or in a few cases, both anteriorly and posteriorly.

In order to carry out such spinal surgery, the surgical area must be of sufficient size to allow the surgeon ample access for carrying out procedures. Many current devices do not permit a surgeon or other qualified professional easy access to a surgical site, and moreover, current devices do not address the clearing of tissue obstructions at deeper levels in the surgical site. Thus, there is a need for a device that can assist a surgeon or other qualified profession in retracting obstructive tissue away from the surgical site.

SUMMARY OF THE INVENTION

Embodiments of the present invention relate to retractor devices, some embodiments of which include a housing, at least one blade holder configured to be radially translatable and/or slidably coupled to the housing, and an actuator handle configured to control sliding movement of the at least one blade holder. The at least one blade holder and the actuator handle are configured to hold at least one blade.

In one alternate embodiment, the retractor includes a plurality of blade holders, which may include a first blade holder, a second blade holder, and a third blade holder. The blade holders may be triangularly (or otherwise) disposed within the housing.

In another embodiment, the present invention relates to a method for retracting body tissue within a body of a patient using a retractor device having a housing with a hollow center portion, three blade holders configured to be radially translatable and/or slidably coupled to the housing, an actuator handle configured to control sliding movement of the blade holders, where each blade holder is configured to hold a blade. The method includes releasing the actuator handle which translates the blade holders towards a center of the hollow center portion of the housing and collapses the blades together. The method may include a step of inserting the collapsed blades into the body tissue selected for retraction, then compressing the actuator handle (e.g., by squeezing by the hand of the surgeon or surgical assistant/nurse). The actuations causes tensioning of a cable system (for example) which radially translates (for example) the blade holders away from the center of the hollow center portion of the housing and pulls the blades apart, resulting in the body tissues being driven apart.

Embodiments of the invention relate to a tissue retractor for use by medical personnel (i.e., doctor) for spinal surgery, and may be used to expose spinal structures during spinal surgery. Such embodiments, for example, enable minimal disruption of spinal muscles and sensitive elements of the posterior, lateral, and anterior regions of the spine. Furthermore, some embodiments of the invention are capable of performing in the thoracolumbar region, as well as sacral and cervical regions of the spine, or any other regions.

Some embodiments of the invention include an open halo structure to form a rigid platform. This open halo may allow for instruments to be manipulated from inside to outside of the halo. The halo may include openings for attaching, for example, a rigid arm to secure the halo, and thus the instrument (according to some embodiments), in place.

In some embodiments of the invention, retraction blades are included in various lengths, configurations, and with various features to accommodate different applications for the retractor. The blades may be used to form a closed exposure to the surgical site and can be installed easily while at this position. The blades may be constructed of various materials to aid in radio translucency, strength, flexibility, and integration with anatomy etc.

Some embodiments of the invention may also include a retraction mechanism which allows a squeezing motion to expand the retractor and expose the desired spinal elements. Such a ratcheting mechanism allows for incremental expansion of the retraction blades. In that regard, the expansion load may be transmitted from the handle to the blades by a cable, which may be woven through the mechanism. The characteristics of the cable allow loads to be compounded and increased. Specifically, in the cable system, using a system of pulleys, the cable may be directed through the rigid halo structure.

Some embodiments of the invention include a plurality of cables, and in some embodiments, three (3) cables. For each cable, a free end may be attached to the rigid halo and the other may be attached to a spool that is driven by the handle. The spool may incorporate different diameters for different cables and thus may yield different retraction rates.

Further features and advantages of the invention, as well as structure and operation of various embodiments of the invention, are disclosed in detail below with references to the accompanying drawings.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE INVENTION

Figure 1:
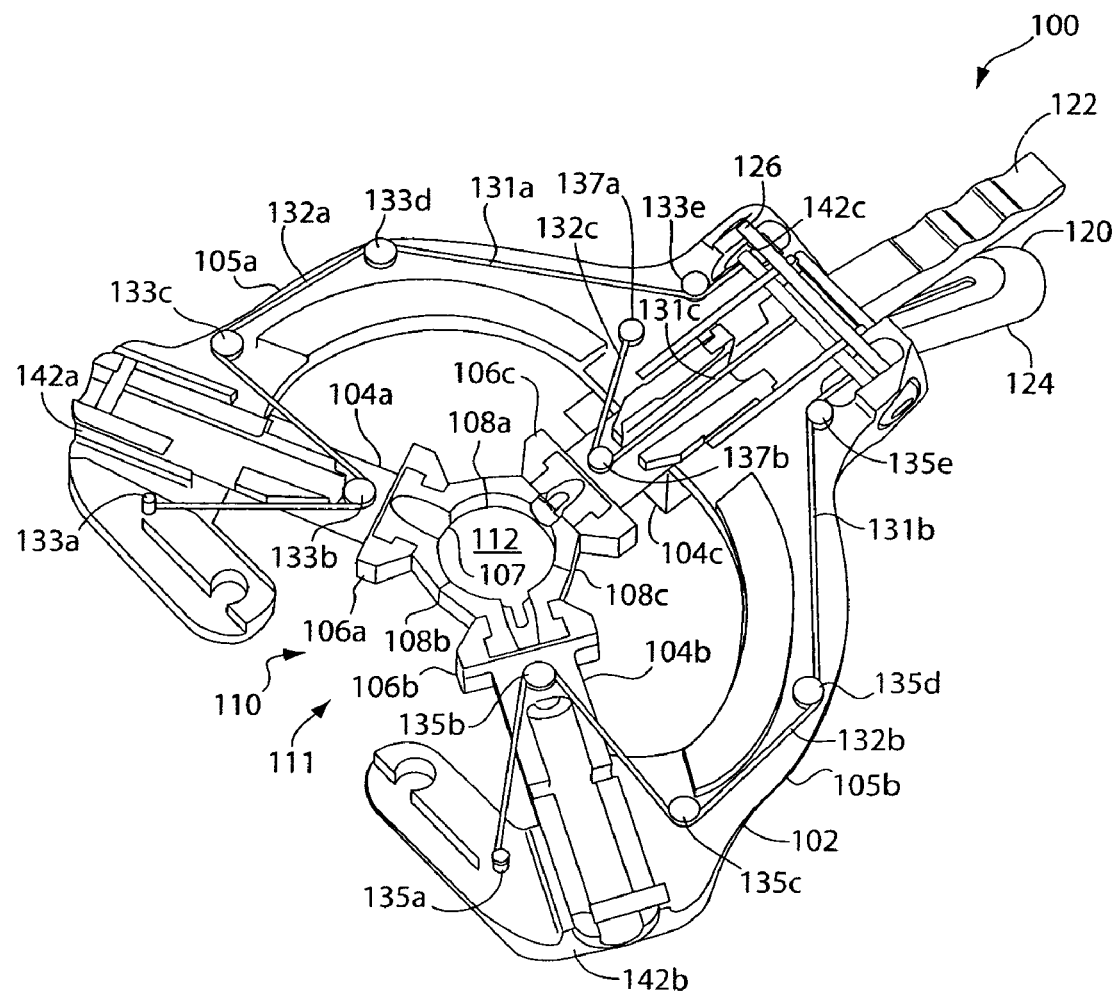
FIG. 1 is a perspective, cross-sectional view of a retractor device according to one embodiment of the present invention.

FIG. 1 is a perspective, cross-sectional bottom view of a retractor device 100 which includes a housing 102, a handle assembly 120, three blade holders 104(a, b, c), and three blades 108(a, b, c). As can be understood by one skilled in the art, there can be any number of blade holders 104 and blades 108.

The housing 102 further includes a hollow interior or a halo 110 formed by the sides 105(a, b). The sides 105(a, b) are joined together at the handle assembly 120 and form a gap 111 opposite the handle assembly 120. As can be understood by one skilled in the art, the sides 105 can be joined together at all times and not form any gaps. The hollow interior 110 further includes a center 112 that is located substantially in the center of the hollow interior 110.

As shown in FIG. 1, the blade holders 104 are configured to be slidably coupled to the housing 102, which allows the blade holders 104 to be capable of translational movement within the same plane as the plane of the housing 102. The movement of the blade holders 104 is configured to be within the hollow interior 110 and to and/or from (or away from) the center 112 (i.e., radially). The housing 102 further includes channels 142(a, b, c) that are configured to hold the blade holders 104 and allow such translational movement of the blade holders 104. The channels 142 are further configured to be aligned in a direction of the center 112, thereby allowing blade holders 104's translational movement.

The handle assembly includes a permanent handle 124 and an actuating handle 122. The permanent handle 124 may be rigidly coupled to the housing 102. In one embodiment, the permanent handle 124 may be permanently coupled to the sides 105. The actuating handle 122 is pivotally coupled to a spool mechanism 126, which, in turn, may be coupled to the sides 105 and/or to the permanent handle 124. The spool mechanism 126 is configured to allow actuating handle 122 to at least partially pivot to and from the permanent handle 124. The handle assembly 120 is further configured to be coupled to a plurality of cable systems 131(a, b, c). The spool mechanism 126 can be a catch-and-release mechanism (e.g., ratchet type) that is configured to pull cables when the mechanism is actuated by a handle and release cables when the handle is released. This mechanism may include a spring-loaded device and a stopper device that allow pulling and releasing of the cables. As can be understood by one skilled in the art, other mechanisms and methods of pulling/tensioning and releasing the cables may be used.

The cable system 131a is configured to connect the handle assembly 120 and the first blade holder 104a. The cable system 131b is configured to connect the handle assembly 120 and the second blade holder 104b. The cable system 131c is configured to connect the handle assembly 120 and the third blade holder 104c.

The cable system 131a further includes a cable 132a and a plurality of pins 133(a, b, c, d, e). The cable 132a is configured to be permanently secured to the pin 133a on the housing 105a as well as to be permanently secured to the spool mechanism 126 of the handle assembly 120. The cable 132a forms a sliding or a rolling connection with other pins 133(b, c, d, e), including the pin 133b located on the blade holder 104a. The pins 133a, 133b, and 133c form a triangular composition that allows translational movement of the blade holder 104a. The pins 133d, 133e allow the cable 132a to be strung around the side 105a so as to prevent interference of the cable 132a with other components of the retractor device 100 as well as patient's body tissue which is selected for retraction.

The cable system 131b may further include a cable 132b and a plurality of pins 135(a, b, c, d, e). The cable 132b is configured to be permanently secured to the pin 135a on the housing 105b as well as to be permanently secured to the spool mechanism 126 of the handle assembly 120. The cable 132b forms a sliding or a rolling connection with other pins 135(b, c, d, e), including the pin 135b located on the blade holder 104b. The pins 135a, 135b, and 135c form a triangular composition that allows translational movement of the blade holder 104b. The pins 135d, 135e allow the cable 132b to be strung around the side 105b so as to prevent interference of the cable 132b with other components of the retractor device 100 as well as patient's body tissue which is selected for retraction.

The cable system 131c further includes a cable 132c and pins 137(a, b). The cable 132c may be configured to be permanently secured to the pin 137a on the housing 105a as well as to be permanently secured to the spool mechanism 126 of the handle assembly 120. The cable 132c forms a sliding or a rolling connection with pin 137b located on the blade holder 104c. The pins 137a and 137b form an angular composition that allows translational movement of the blade holder 104c. The pins 137a and 137b allow the cable 132c to be strung around the side 105a so as to prevent interference of the cable 132c with other components of the retractor device 100 as well as patient's body tissue which is selected for retraction.

As stated above, the cable systems 131 may be configured to allow translational movement of the blade holders 104, i.e., movement to and from the center 112 of the hollow interior 110. The blade holders 104 may be configured to be disposed within the housing in a triangular fashion. As can be understood by one skilled in the art, the blade holders 104 can be disposed in any other fashion, corresponding to the number and position of the blade holders used. To translate the blade holders 104 away from the center 112, the actuating handle 122 is forced towards the permanent handle 124 of the handle assembly 120 (i.e., squeezed). This causes cable systems 131 to tension and pull the cables 132 towards the spool mechanism 126. Once cable 132a is pulled, the triangular arrangement of pins 133 (a, b, c) forces the blade holder 104a to pull away radially from the center 112. Similarly, once the cable 132b is pulled, the triangular arrangement of pins 135(a, b, c) forces the blade holder 104b to radially pull away from the center 112. Also, once the cable 132c is pulled, the angular arrangement of pins 137(a, b) forces the blade holder 104c to radially pull away from the center 112. As can be understood by one skilled in the art, the pulling of each blade holder 104 can be simultaneous or selective (preferably, simultaneous). Further, the blade holders 104 can be pulled from the center 112 all the way to the sides 105 either in one application of forcing the handle 122 to the handle 124 or in several applications (i.e., gradually). The releasing of the blade holders 104 can be done in a similar fashion, but in a reverse order, i.e., releasing the handle 122 to release blade holders 104.

Blade holders 104(a, b, c) may further include blade holder tips 106(a, b, c), respectively. Blade holder tips 106 are configured to couple the blade holders 104 to the blades 108. Thus, the blade holder tip 106a couples the blade holder 104a to the blade 108a; the blade holder tip 106b couples the blade holder 104b to the blade 108b; and the blade holder tip 106c couples the blade holder 104c to the blade 108c. In one embodiment, the blade holder tips 106 may be configured to receive blades 108 and secure the blades 108 inside the tips 106. The blade holder tips are further configured to allow doctors (or other qualified professionals) to exchange one set of blades 108 for another, if such exchange is desired. The blades 108 and the tips 106 can be frictionally fit together or a locking mechanism can be used to secure the blades 108 and the tips 106. In an alternate embodiment, the tips 106 and/or blade holders 104 can also be interchangeable, as desired.

As shown in FIG. 1, once the blade holders 104 are released, the blades 108 are pushed together towards the center 112. In the illustrated embodiments, the combination of the three released blades 108 forms a circle. As can be understood by one skilled in the art, the combination of the released blades can form any other shape, such as square, rectangle, polygon, oval, or any other regular or irregular shape. As can be further understood by one skilled in the art, there can be any number of blade holders 104, blade holder tips 106, and blades 108 coupled to the housing. The blades 108 along with corresponding holding mechanisms may be added or removed as desired. Also, the blades 108 can have any size shape, thickness, material or have any other parameters.

Figure 2:
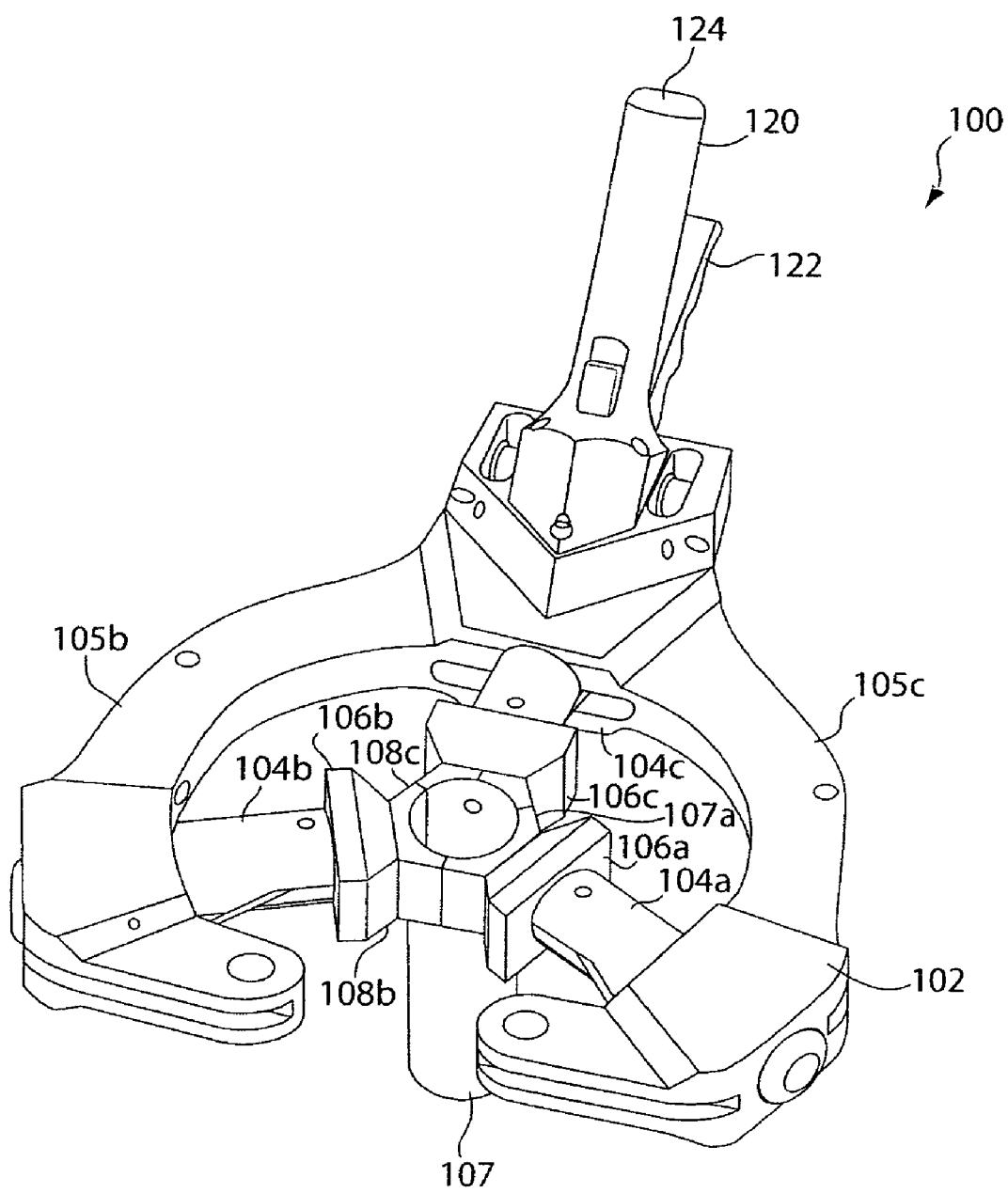
FIG. 2 is a top, perspective view of a retractor device according to one embodiment of the present invention.
Figure 3:
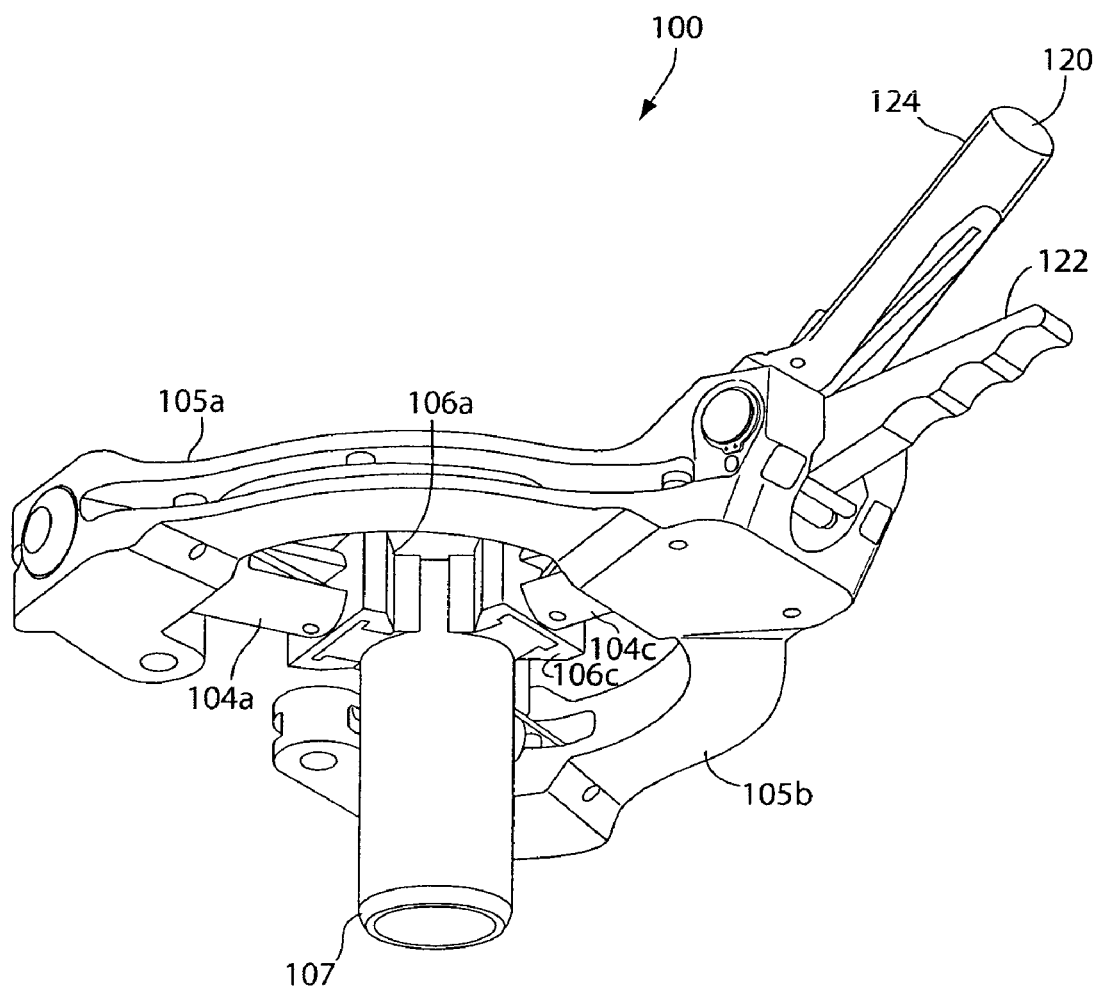
FIG. 3 is a bottom, perspective view of a retractor device according to one embodiment of the present invention.

Referring to FIGS. 2-3, the blades 108 can have any length, width or shape. Specifically, FIG. 2, which is a top perspective view of the retractor 100, illustrates that the combination of released blades 108 forms a hexagon-shaped cylinder. Alternatively, FIG. 3, which is a bottom perspective view of the retractor 100, illustrates that the combination of released blades 108 forms a regular cylinder.

As further illustrated in FIGS. 1-3, the sides 105(a, b) can be multi-layered, thereby allowing placement of cable systems 131 between the layers. This prevents interferences of the cable systems 131 during application of the retractor device 100 on the patient.

Figure 4:
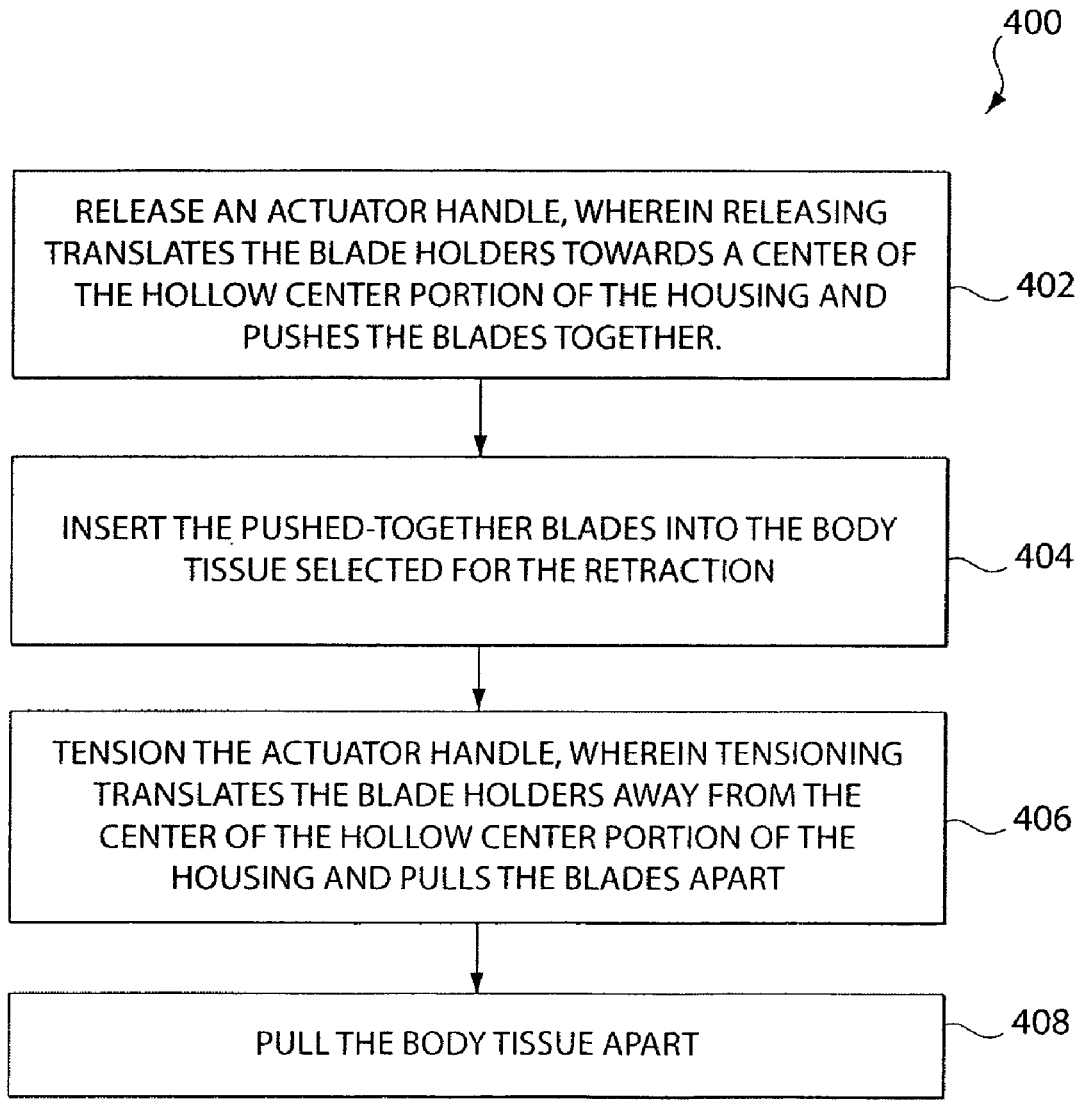
FIG. 4 is a flow chart illustrating an exemplary method for retracting body tissue using a retractor device, according to the present invention.

FIG. 4 illustrates a method 400 for retracting a body tissue within a body of a patient using a retractor device 100, illustrated in FIGS. 1-3. In step 402, the retractor blades 108 are released to allow the blades 108 to be pushed together towards the center 112 of the hollow center portion 110. In one embodiment, the step 402 is performed if the blades 108 are in a tensioned state, i.e., pulled away from the center 112.

In step 404, the retractor device 100, having blades 108 pushed together towards the center 112, is placed on the patient at a location where bodily tissue needs to be retracted. This location can be any location on or within the body, such as a location where a surgical procedure is being or will be performed. In an embodiment, the retractor device can be used to expose spinal structures during spinal surgery. This allows for minimal disruption of spinal muscles and sensitive elements of the posterior, lateral, and anterior regions of the spine. The retractor device 100 can also be used in the thoracolumbar region, as well as, sacral and cervical regions of the spine, or any other regions.

In step 406, the handle assembly 120 is used to tension the cables 132 of the cable systems 131. This may be accomplished be forcing the permanent handle 124 and the actuator handle 122 together (i.e., squeezing them together). Once the cables 132 are tensioned, the blade holders 104 slide or translate along the channels 142 away from the center 112 of the hollow portion 110. Once the blade holders 104 begin to slide, the blades 108 begin moving away from the center 112 as well and engage bodily tissue coming in contact with the blades 108. By forcing the blades 108 apart, the engaged bodily tissue are also spread/forced apart, as illustrated in step 408. As stated above, this exposes the bodily regions on which a surgical procedure may be performed. Also, by spreading the tissue apart, the surgeon (or other qualified professional) can easily move in and out any surgical tools needed for performing the surgical procedure.

As can be understood by one skilled in the art, the retractor device 100 and/or any of its components may have any size, shape, length, thickness, height, weight, or any other parameters. Such parameters may be selected by the surgeon (or other qualified professional) for performance of specific procedures. Further, the retractor device 100 and/or any of its components may be manufactured from metal, plastic, synthetic material, or other suitable materials, or any combination thereof.

Further, the blade holders 104 along with blades 108 can be gradually retracted or translated along the channels 142 to slowly retract the obstructive bodily tissue away from the surgical site. Alternatively, the blade holders 104 along with blades 108 can be instantaneously retracted or translated along the channels 142 to quickly retract such bodily tissue. As can be understood by one skilled in the art, the handle assembly 120 can include a stepping mechanism (not shown in FIG. 1) in combination with the spool mechanism 126 that allows gradual retraction of the blades 108. This allows a surgeon (or other qualified professional) to retract the obstructive tissue step by step and prevent any accidental injury to the sensitive bodily tissues.

Example embodiments of the methods and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. A retractor, comprising:
a housing;
a plurality of blade holders comprising a first blade holder, a second blade holder, and a third blade holder, wherein said blade holders are radially disposed within said housing and configured to be slidably coupled to said housing; and
an actuator handle coupled to a spool mechanism comprising a first cable system having at least one cable configured to control movement of said first blade holder, a second cable system having at least one cable to control translational movement of said second blade holder, and a third cable system having at least one cable configured to control translational movement of said third blade holder; wherein
said at least one blade holder is configured to hold at least one blade;
said at least one blade holder includes a blade holder tip configured to allow exchange of said at least one blade with another blade;
said at least one blade holder and blade holder tip are interchangeable.

2. The retractor according to claim 1, wherein said spool mechanism is configured to be controlled by said actuator handle.

3. The retractor according to claim 1, wherein at least one of said cable systems are configured to be controlled by said actuator handle.

4. The retractor according to claim 1, wherein said actuator handle is configured to control tension of one or more cables of said cable system upon the compression of said actuator causing said blade holders to retract away from a center of said housing.

5. The retractor according to claim 1, wherein said blade holders are configured to be at least partially disposed within said hollow center portion and are further configured to radially translate within said hollow center portion.

6. The retractor according to claim 1, further comprising a plurality of blades, each for a respective blade holder, said blades are configured to move with said blade holders and configured to spread body tissue within a body of a patient apart upon actuation of the actuation holder.

7. The retractor according to claim 1, wherein said blade holders are configured to uniformly move in unison within said housing.

8. A method for retracting body tissue within a body of a patient using a retractor device having
a housing with a hollow center portion,
a plurality of radially spaced apart blade holders having corresponding blades, wherein the blade holders are configured to slidably coupled to the housing,
an actuator handle, coupled to a spool mechanism having at least one cable coupled to the at least one blade holder, and configured to control translational movement of the blade holders within hollow center portion of the housing, wherein each blade holder is configured to hold a blade and the at least one blade holder includes a blade holder tip configured to allow exchange of the at least one blade with another blade; wherein the at least one blade holder and blade holder tip are interchangeable, the method comprising the steps of:
releasing the actuator handle, wherein said releasing translates the blade holders towards a center of the hollow center portion of the housing and forces the blades together;
inserting the pushed-together blades into the body tissue selected for retraction;
compressing the actuator handle, wherein said compression translates the blade holders away from the center of the hollow center portion of the housing and radially translates the blades apart resulting in the blades being spread apart from the center of the hollow center portion of the housing spreading of body tissue apart.

9. The method according to claim 8, wherein said releasing further comprises lessening tension in the at least one cable and causing the blade holders to move toward the center of the center portion of the housing.

10. The method according to claim 8, wherein said tensioning further comprises increasing tension in the at least one cable and causing the blade holders to retract away from the center of the center portion of the housing.

11. The method according to claim 8, wherein the blade holders are configured to be at least partially disposed within the hollow center portion of the housing and are further configured to radially translate within the hollow center portion.

12. The method according to claim 8, further comprising uniformly moving the blade holders in unison within the housing.

13. The method according to claim 8, further comprising non-uniformly moving the blade holders within the housing.

* * * * *